(12) United States Patent
Consoli et al.

(10) Patent No.: US 9,993,413 B2
(45) Date of Patent: Jun. 12, 2018

(54) KERATIN FIBRE DYEING COMPOSITION

(71) Applicant: BEAUTY & BUSINESS S.p.A., Milan (IT)

(72) Inventors: Antonio Consoli, Urgnano (IT); Katiuscia Grevalcuore, Bergamo (IT); Emanuela Facchetti, Romano di Lombardia (IT)

(73) Assignee: BEAUTY & BUSINESS S.P.A., Milan (IT)

( * ) Notice: Subject to any disclaimer, the term of this patent is extended or adjusted under 35 U.S.C. 154(b) by 0 days. days.

(21) Appl. No.: 15/440,020

(22) Filed: Feb. 23, 2017

(65) Prior Publication Data
US 2017/0258695 A1 Sep. 14, 2017

(30) Foreign Application Priority Data

Mar. 9, 2016 (IT) .................. 102016000024860

(51) Int. Cl.
*A61Q 5/10* (2006.01)
*A61K 8/55* (2006.01)
*A61K 8/39* (2006.01)
*A61Q 5/06* (2006.01)

(52) U.S. Cl.
CPC .................. *A61K 8/55* (2013.01); *A61K 8/39* (2013.01); *A61Q 5/065* (2013.01); *A61Q 5/10* (2013.01); *A61K 2800/4324* (2013.01)

(58) Field of Classification Search
CPC . A61Q 5/10; A61Q 5/065; A61K 8/22; A61K 8/55
See application file for complete search history.

(56) References Cited

U.S. PATENT DOCUMENTS

2003/0226217 A1    12/2003  Bowes et al.
2014/0338135 A1*   11/2014  Kim .................. A61K 8/33
                                               8/406

FOREIGN PATENT DOCUMENTS

EP    2033625 A1    3/2009
EP    2979683 A1    2/2016

OTHER PUBLICATIONS

International Cosmetic Ingredient Dictionary and Handbook (Jul. 31, 2014).*
"Potassium Ethylhexyl/Isotriceceth-8 Phosphate"; "INCI Name Monographs I—S" In: "International Cosmetic Ingredient Dictionary and Handbook", Jul. 31, 2014 vol. 2, p. INCI Monograph ID: 28057.
Search Report and Written Opinion of Italian Application IO 62939 IT UA20161510 of Jul. 11, 2016.

* cited by examiner

*Primary Examiner* — Eisa B Elhilo
(74) *Attorney, Agent, or Firm* — Silvia Salvadori, P.C.; Silvia Salvadori

(57) ABSTRACT

Disclosed are compositions for dyeing keratin fibers comprising at least one direct dye and/or an oxidative dye and optionally an activator, and also comprising a compound formed by esterification of phosphoric acid with isooctanol (2-ethylhexanol) and ethoxylated tridecylic alcohol.

5 Claims, No Drawings

KERATIN FIBRE DYEING COMPOSITION

This U.S. Non-Provisional application claims priority to and the benefit from Italian Patent Application No. 102016000024860 filed on Mar. 9, 2016, the content of which is incorporated herein by reference in its entirety.

The invention relates to compositions for dyeing keratin fibers comprising at least one direct dye and/or an oxidative dye and optionally an activator, and also comprising a compound formed by esterification of phosphoric acid with isooctanol (2-ethylhexanol) and ethoxylated tridecylic alcohol.

PRIOR ART

There are currently numerous trends in hair dyeing. In the past, the hair was mainly dyed to conceal areas of grey hair, whereas there is now increased demand for fashionable hair colors. Two hair dyeing technologies are widely used. The first involves the use of oxidative dyes and an activator (oxidative hair dyes), while the second involves the use of direct dyes.

Oxidative dyes have become very important in the conventional hair dye field. The color is created by the reaction of primary intermediates and couplers in the presence of an oxidant. Oxidative dyes give the best performance in terms of resistance to washing, and are therefore called permanent hair dyes.

Direct dyes have become widely used in recent years because oxidative dyes have led to an increase in sensitization problems, and cannot be used to create very bright tones. Particular combinations of Magenta, Blue and Yellow can be used to produce "crazy" shades like violet, red, purple and green, or natural shades like black, brown, gold and copper.

Direct dyes can be classified as anionic, cationic and non-ionic.

The hair tints that can be created with direct dyes can be classified, according to their ability to withstand washing, as semipermanent or temporary. Semipermanent hair dyes can withstand up to 8 washes, and temporary dyes up to 2 washes (see Table A), The tints available to hairdressers consist of combinations of dyes defined as secondary colors, which are usually called shades. The International Color Chart (ICC) is a system used to classify hair tints. This means that every dye has a code defining its color. Said code can be used by manufacturers of color charts or tints. In practice, the ICC system uses numbers to define the depth (level) and tone of a given color.

The color level indicates how light or dark the shade is. The ICC system assigns a number to measure the level of lightness or darkness. Said values range from 1 to 10, wherein 1 denotes the darkest shade (black) and 10 the lightest shade (lightest blonde). Some manufacturers also use the codes 11 and 12 on their hair dyeing products to indicate platinum blonde shades. The usual level numbers and names are as follows:

TABLE B

| Level | Level name |
| --- | --- |
| 1 | Black |
| 2 | Very dark brown |
| 3 | Dark brown |
| 4 | Medium brown |
| 5 | Light brown |
| 6 | Dark blonde |
| 7 | Medium blonde |
| 8 | Light blonde |
| 9 | Very light blonde |
| 10 | Lightest blonde |
| 11 | Platinum blonde |

The tone indicates how cool or warm a color is, and includes colors such as gold, ash and copper.

Although the level measurement is almost identical for all manufacturers, each manufacturer can vary the tone number at its discretion. Tone is indicated by a number, usually placed after the level, separated by a decimal point ".", a comma "," or a slash "/". The classification used by the Applicant is set out below by way of example

TABLE C

| Tone number | Tone name |
| --- | --- |
| 0 | Natural (grey-neutral) |
| 1 | Ash (blue) |

TABLE A

|  | Temporary | Semipermanent | Demipermanent | Permanent |
| --- | --- | --- | --- | --- |
| DURABILITY PROPERTIES | 1-2 shampoos | 6-8 shampoos | 6-8 weeks | Permanent |
| LIGHTENING EFFECT | No | No | No | Yes |
| COVERING GREY HAIR | No | For people with a maximum of 30% grey hair (early greying) | For people with a maximum of 50% grey hair | For people with 100% grey hair |
| COLOUR PROPERTIES | Only on decolored hair, or to add some tones | All levels with or without decolorant; if used without decolorant, a secondary tone is obtained | All levels with or without decolorant | Lighter, identical or darker levels With/without highlights |
| FINISHED PRODUCT | Ready to use | Ready to use | Mix before use: 1 colored product + 1 to 3 parts activator. | Mix before use: 1 colored product + 1 to 3 parts activator. |

TABLE C-continued

| Tone number | Tone name |
|---|---|
| 2 | Irisé (violet) |
| 3 | Gold (yellow) |
| 4 | Copper (orange) |
| 5 | Mahogany (violet red) |
| 6 | Red (red) |
| 7 | Matte (green) |
| 8 | Pearl |

Some hair tints can have a double tone, and it is usual to place two numbers after the decimal point of the level to express said characteristic. For example, if the color chart contains the number 7.21, the first number indicates the medium blonde level (7), the second indicates the irisé tone (2), and the third number indicates a secondary blue ash tone (1). Said color will be called "medium blonde irisé ash".

Cosmetics manufacturers are always searching for ingredients able to give the best results in terms of evenness of color and resistance to washing.

Uneven color occurs when the lengths or ends of the hair are treated differently from the regrowth. This mainly takes place when the lengths are particularly damaged by bleaching treatments, permanent waves or exposure to UV rays.

An artificial hair dye must withstand washing as far as possible without fading or changing color.

The purpose of the invention is to solve these problems with a novel composition that increases the duration of resistance to washing and gives a more even color from root to tip.

DESCRIPTION OF THE INVENTION

It has been found that said purposes are achieved by a composition comprising at least one direct dye and/or an oxidative dye and possibly an activator, and also including a compound formed by esterification of phosphoric acid with isooctanol (2-ethylhexanol) and ethoxylated tridecylic alcohol.

Examples of oxidative dyes (component A), defined according to the INCI nomenclature (European Community Decision 2006/257/EC as amended—International Nomenclature of Cosmetic Ingredients), include:

1-Acetoxy-2-Methylnaphthalene, 5-Amino-4-Chloro-o-Cresol, 4-Amino-m-Cresol, 6-Amino-m-Cresol, 3-Amino-2,4-Dichlorophenol, 6-Amino-2,4-Dichloro-m-Cresol, 3-Amino-2,4-Dichlorophenol, 5-Amino-2,6-Dimethoxy-3-Hydroxypyridine, 5-Amino-2,6-Dimethoxy-3-Hydroxypyridine, 3-Amino-2,6-Dimethylphenol, 2-Amino-5-Ethylphenol, 5-Amino-4-Fluoro-2-Methylphenol Sulfate, 2-Amino-4-Hydroxyethylaminoanisole, 2-Amino-4-Hydroxyethylaminoanisole, 2-Amino-3-Hydroxypyridine, 4-Amino-2-Hydroxytoluene, 2-Aminomethyl-p-Aminophenol, 4-Amino-2-Nitrodiphenylamine-2'-Carboxylic Acid, m-Aminophenol, o-Aminophenol, p-Aminophenol, 1,3-Bis-(2,4-Diaminophenoxy)propane, 4,6-Bis(2-Hydroxyethoxy)-m-Phenylenediamine, 2,6-Bis(2-Hydroxyethoxy)-3,5-Pyridinediamine, N,N-Bis(2-Hydroxyethyl)-p-Phenylenediamine, 4-Chloro-2-Aminophenol, 2-Chloro-p-Phenylenediamine, 4-Chlororesorcinol, N-Cyclopentyl-m-Aminophenol, 3,4-Diaminobenzoic Acid, 4,5-Diamino-1-((4-Chlorophenyl)Methyl)-1H-Pyrazole-Sulfate, 2,3-Diaminodihydropyrazolo Pyrazolone Dimethosulfonate, 2,4-Diaminodiphenylamine, 4,4'-Diaminodiphenylamine, 2,4-Diamino-5-Methylphenetole, 2,4-Diamino-5-Methylphenoxyethanol, 4,5-Diamino-1-Methylpyrazole, 2,4-Diaminophenol, 2,4-Diaminophenoxyethanol, 2,6-Diaminopyridine, 2,6-Diamino-3-((Pyridin-3-yl)Azo)Pyridine, N,N-Diethyl-m-Aminophenol, N,N-Diethyl-p-Phenylenediamine, N,N-Diethyltoluene-2,5-Diamine, 2,6-Dihydroxy-3,4-Dimethylpyridine, 2,6-Dihydroxyethylaminotoluene, Dihydroxyindole, Dihydroxyindoline, 2,6-Dimethoxy-3,5-Pyridinediamine, m-Dimethylaminophenyl Urea, N,N-Dimethyl-p-Phenylenediamine, 2,6-Dimethyl-p-Phenylenediamine, N,N-Dimethyl 2,6-Pyridinediamine, 4-Ethoxy-m-Phenylenediamine, 3-Ethylamino-p-Cresol, 4-Fluoro-6-Methyl-m-Phenylenediamine, 1-Hexyl 4,5-Diamino Pyrazole Sulfate, Hydroquinone, Hydroxyanthraquinoneaminopropyl Methyl Morpholinium Methosulfate, Hydroxybenzomorpholine, Hydroxyethoxy Aminopyrazolopyridine, Hydroxyethylaminomethyl-p-Aminophenol, 1-Hydroxyethyl 4,5-Diamino Pyrazole, Hydroxyethyl-2,6-Dinitro-p-Anisidine, Hydroxyethyl-3,4-Methylenedioxyaniline, Hydroxyethyl-p-Phenylenediamine, 2-Hydroxyethyl Picramic Acid, 6-Hydroxyindole, Hydroxypropyl Bis(N-Hydroxyethyl-p-Phenylenediamine), Hydroxypropyl-p-Phenylenediamine, Hydroxypyridinone, Isatin, N-Isopropyl 4,5-Diamino Pyrazole, N-Methoxyethyl-p-Phenylenediamine, 6-Methoxy-2-methylamino-3-aminopyridine, 2-Methoxymethyl-p-Aminophenol, 2-Methoxymethyl-p-Phenylenediamine, 2-Methoxy-p-Phenylenediamine, 6-Methoxy-2,3-Pyridinediamine, 4-Methoxytoluene-2,5-Diamine, p-Methylaminophenol, 4-Methylbenzyl 4,5-Diamino Pyrazole, 2,2'-Methylenebis 4-Aminophenol, 3,4-Methylenedioxyaniline, 3,4-Methylenedioxyphenol, 2-Methyl-5-Hydroxyethylaminophenol, Methylimidazoliumpropyl p-Phenylenediamine, 2-Methyl-1-Naphthol, 2-Methylresorcinol, 1,5-Naphthalenediol, 1,7-Naphthalenediol, 2,3-Naphthalenediol, 2,7-Naphthalenediol, 1-Naphthol, 2-Naphthol, PEG-3 2,2'-Di-p-Phenylenediamine, p-Phenetidine, m-Phenylenediamine, p-Phenylenediamine, Phenyl Methyl Pyrazolone, N-Phenyl-p-Phenylenediamine, Picramic Acid, Pyrocatechol, Pyrogallol, Resorcinol, Sodium Picramate, Tetraaminopyrimidine, Tetrahydro-6-Nitroquinoxaline, Tetrahydropyranyl, Resorcinol, Toluene-2, 5-Diamine, Toluene-2,6-Diamine, Toluene-3,4-Diamine, 2,5,6-Triamino-4-Pyrimidinol, 1,2,4-Trihydroxybenzene. The oxidative dyes can be in the form of salts.

The total quantity of the combination of primary dyes and couplers in the dye according to the invention preferably ranges between about 0.001 and 20% by weight, more preferably between about 0.002 and 10% by weight, and even more preferably between about 0.01 and 6.0% by weight.

When the dye is mixed with the activator, which in most cases is acidic (pH about 2 to 6.5), the pH of the ready-to-use hair tints according to the invention acquires a value determined by the quantity of alkali in the dye and the quantity of acid in the oxidant, and by the mixing ratio. Depending on their composition, the ready-to-use hair tints according to the invention can be weakly acidic, neutral or alkaline, and have a pH ranging from about 3 to 11, preferably from 6.5 to 11.

"Activator" means hydrogen peroxide, carbamide peroxide, perborates and persulfates or peracids, preferably hydrogen peroxide. The quantity can range from 0.1 to 50%.

Examples of direct dyes (component B), defined according to the INCI nomenclature (European Community Decision 2006/257/EC as amended—International Nomenclature of Cosmetic Ingredients), include:

Acid green 25, Acid blue 74, Acid blue 3, Acid blue 9, Acid red 18, Acid red 184, Acid red 195, Acid red 27, Acid red 33, Acid red 35, Acid red 51, Acid red 73, Acid red 87, Acid red 92, Acid red 95, Acid violet 43, Acid violet 9, Acid yellow 23, Acid yellow 3, Acid yellow 36, Acid yellow 73, Acid orange 6, Acid orange 7, Acid green 1, Acid green 50, Acid Blue 1, Acid Blue 62, Acid Brown 13, Acid Orange 3, Acid Orange 24, Acid Red 14, Acid Red 35, Acid Red 52, Acid Yellow 1, 2-Amino-6-Chloro-4-Nitrophenol, 4-Amino-2-Nitrodiphenylamine-2'-Carboxylic Acid, 2-Amino-3-Nitrophenol, 2-Amino-4-Nitrophenol, 2-Amino-5-Nitrophenol, 4-Amino-2-Nitrophenol, 4-Amino-3-Nitrophenol, Basic Blue 3, Basic Blue 7, Basic Blue 9, Basic Blue 26, Basic Blue 47, Basic Blue 75, Basic Blue 99, Basic Blue 124, Basic Brown 4, Basic Brown 16, Basic Brown 17, Basic Green 1, Basic Green 4, Basic Orange 1, Basic Orange 2, Basic Orange 31, Basic Red 1, Basic Red 1:1, Basic Red 2, Basic Red 22, Basic Red 46, Basic Red 51, Basic Red 76, Basic Red 118, Basic Violet 1, Basic Violet 2, Basic Violet 3, Basic Violet 4, Basic Violet 10, Basic Violet 11:1, Basic Violet 14, Basic Violet 16, Basic Yellow 28, Basic Yellow 40, Basic Yellow 57, Basic Yellow 87, N,N'-Bis(2-Hydroxyethyl)-2-Nitro-p-Phenylenediamine, 2-Chloro-6-Ethylamino-4-Nitrophenol, 2-Chloro-5-Nitro-N-Hydroxyethyl p-Phenylenediamine, N,N'-Dimethyl-N-Hydroxyethyl-3-Nitro-p-Phenylenediamine, Direct Black 51, Direct Red 23, Direct Red 80, Direct Red 81, Direct Violet 48, Direct Yellow 12, Disperse Black 9, Disperse Blue 1, Disperse Blue 3, Disperse Blue 7, Disperse Blue 377, Disperse Brown 1, Disperse Orange 3, Disperse Red 11, Disperse Red 15, Disperse Red 17, Disperse Violet 1, Disperse Violet 4, Disperse Violet 15, HC Blue No. 2, HC Blue No. 4, HC Blue No. 5, HC Blue No. 6, HC Blue No. 8, HC Blue No. 9, HC Blue No. 10, HC Blue No. 11, HC Blue No. 12, HC Blue No. 13, HC Blue No. 14, HC Blue No. 15, HC Blue No. 16, HC Blue No. 17, HC Blue No. 18, HC Brown No. 1, HC Brown No. 2, HC Green No. 1, HC Orange No. 1, HC Orange No. 2, HC Orange No. 3, HC Orange No. 5, HC Orange No. 6, HC Red No. 1, HC Red No. 3, HC Red No. 7, HC Red No. 8, HC Red No. 9, HC Red No. 10, HC Red No. 11, HC Red No. 13, HC Red No. 14, HC Red No. 15, HC Red No. 17, HC Red No. 18, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, HC Yellow No. 16, HC Yellow No. 17, 2-Hydroxyethylamino-5-Nitroanisole, Hydroxyethyl-2-Nitro-p-Toluidine, 4-Hydroxypropylamino-3-Nitrophenol, 3-Methylamino-4-Nitrophenoxyethanol, 3-Nitro-4-Aminophenoxyethanol, 3-Nitro-p-Cresol, 2-Nitro-5-Glyceryl Methylaniline, 4-Nitroguaiacol, 3-Nitro-p-Hydroxyethylaminophenol, 2-Nitro-N-Hydroxyethyl-p-Anisidine, Nitrophenol, 4-Nitrophenyl Aminoethylurea, 4-Nitro-o-Phenylenediamine, 4-Nitro-m-Phenylenediamine, 4-Nitro-o-Phenylenediamine, 2-Nitro-p-Phenylenediamine, 6-Nitro-2,5-Pyridinediamine, 6-Nitro-o-Toluidine, Pigment Blue 15, Pigment Blue 15:1, Pigment Violet 23, Pigment Yellow 13, Solvent Black 3, Solvent Black 5, Solvent Blue 35, Solvent Yellow 85, Solvent Yellow 172, Tetrabromophenol Blue, Tetrahydro-6-Nitroquinoxaline, Tetrahydropyranyl Resorcinol.

The dyes described in WO 2014202152 can also be used.

The total quantity of direct dye in the dye according to the invention preferably ranges between about 0.001 and 20% by weight, more preferably between about 0.002 and 10% by weight, and even more preferably between about 0.01 and 6.0% by weight.

Examples of natural direct dyes include those based on lawsone, juglone, alizarin, purpurin, carminic acid, kermesic acid, purpurogallin, protocatechualdehyde, indigo, isatin, curcumin, spinulosine and apigenidine. Extracts or decoctions containing said natural dyes and, in particular, henna-based packs or extracts, can also be used.

The compound formed by esterification of phosphoric acid with isooctanol and ethoxylated tridecylic alcohol, defined according to the INCI nomenclature as Potassium Ethylhexyl/Isotrideceth-8 Phosphate, is present in quantities ranging from 0.1 to 20% by weight, preferably from 0.2 to 10% by weight.

The composition can also include a pH adjuster selected, for example, from ammonia, monoethanolamine (MEA), 1-amino-2-propanol, 2-amino-2-methyl-propanol (AMP), 2-amino-2-methyl-1,3-propanediol, 2-amino-2-ethyl-1,3-propanediol, tris(hydroxymethyl)-aminomethane (tromethamine, Tris), sodium hydroxide, potassium hydroxide, urea, allantoin, arginine, tripotassium phosphate, sodium saccharine, triethanolamine (TEA), lactic acid, citric acid, phosphoric acid or combinations thereof.

The quantity of pH adjuster can range between 0.1 and 20% by weight, preferably between 0.2 and 10% by weight.

The alkanolamine can be present in free-base form or salt form.

The composition can also contain, depending on the tints used, reducing agents and antioxidants such as sodium sulfite, sodium metabisulfite, isoascorbic acid and ascorbic acid.

Pigments such as iron oxides, titanium oxides, zinc oxides, chromium oxides, ultramarine, manganese violet and ferric ferrocyanide can also be used according to the invention. Other particular pigments which can be used are those marketed under the names WATERSPERSE® (S.A. COLOR); UNIPURE® (SENSIENT); CELLINI® (BASF); DISTINCTIVE® (RESOURCE OF NATURE); COLORONA® (MERK); and WD (DAITO KASEI).

Said pigments can be included in the composition in quantities ranging from 0.01 to 10% by weight of the total weight of the composition, preferably from 3 to 8%.

The hair tints according to the invention can also contain one or more natural or synthetic additives, commonly used in solutions, creams, emulsions, gels, aerosols, foams, powders and granulates, for example solvents, such as water, low-molecular-weight aliphatic mono- or polyalcohols, esters and ethers thereof, for example alkanols, in particular having 1 to 4 carbon atoms, such as ethanol, n-propanol, isopropanol, butanol and isobutanol; bivalent or trivalent alcohols, in particular having 2 to 6 carbon atoms, such as ethylene glycol, propylene glycol, 1,3-propanediol, 1,4-butanediol, 1,5-pentanediol, 1,6-hexanediol, 1,2,6-hexanetriol, glycerin, diethylene glycol, dipropylene glycol, polyalkylene glycols, such as triethylene glycol, polyethylene glycol, tripropylene glycol and polypropylene glycol; low-molecular-weight alkyl ethers of multivalent alcohols, such as ethylene glycol monomethyl ether, ethylene glycol monoethyl ether, ethylene glycol monopropyl ether or ethylene glycol monobutyl ether, diethylene glycol monomethyl ether or diethylene glycol monoethyl ether, triethylene glycol monomethyl ether or triethylene glycol monoethyl ether; ketones and keto alcohols, in particular having 3 to 7 carbon atoms, such as acetone, methyl ethyl ketone, diethyl ketone, methyl isobutyl ketone, methyl phenyl ketone, cyclopentanone, cyclohexanone and diacetone alcohol; ethers such as dibutyl ether, tetrahydrofuran, dioxane or diisopropylether; esters such as ethyl formate, methyl formate, methyl acetate, ethyl acetate, propyl acetate, butyl acetate, phenyl acetate, ethylene glycol monoethyl ether acetate or acetic acid hydroxyethyl ester; amides such as N-methylpyrrolidone;

and urea, tetramethyl urea and thiodiglycol; together with wetting agents or emulsifiers selected from anionic, cationic, non-ionic, amphoteric or zwitterionic agents, surfactants, such as fatty alcohol sulfates, alkylsulfonates, alkylbenzene sulfonates, alkyltrimethyl ammonium salts, alkylbetaine, α-olefin sulfonates, ethoxylated fatty alcohols, ethoxylated nonylphenols, fatty acid alkanolamines, ethoxylated esters of fatty acids, polyglycol ether sulfates of fatty acids and alkylpolyglycosides; thickeners, such as higher fatty alcohols, starch, cellulose derivatives, vaseline, paraffin oil, fatty acids and other fatty components in emulsified form, water-soluble polymer thickeners, such as natural gums, guar gum, xanthan gum, carob flour, pectin, dextran, agar-agar, amylose, amylopectin, dextrin, synthetic clays or hydrocolloids, such as polyvinyl alcohol; conditioning agents such as lanolin derivatives, cholesterol, pantothenic acid, water-soluble cationic polymers, protein derivatives, provitamins, vitamins, plant extracts, sugar and betaine; auxiliary agents such as electrolytes, antioxidants, sequestering agents, film-forming agents and preservatives, as well as beeswax.

The addition to the dyes of non-ionic and/or anionic surfactants or emulsifiers, such as fatty alcohol sulfates, in particular lauryl sulfate or sodium cocoyl sulfate; ethoxylated fatty alcohol sulfates, in particular sodium lauryl ether sulfates with 2 to 4 molecular units of ethylene oxide, ethoxylated esters of fatty acids, ethoxylated nonylphenols, ethoxylated fatty alcohols, alkylbenzene sulfonates or alkanolamides of fatty acids, in a total quantity preferably ranging from about 0.1 to 30% by weight, more preferably from 0.2 to 15% by weight, can be particularly advantageous in this case.

Examples of useful cationic surfactants are quaternary ammonium compounds; ammonium halides such as alkyltrimethylammonium chlorides, dialkyldimethylammonium chlorides and trialkylmethylammonium chlorides. Specific examples are cetyltrimethylammonium chloride, stearyltrimethylammonium chloride, di stearyldimethylammonium chloride, lauryldimethylammonium chloride, lauryldimethylbenzylammonium chloride and tricetylmethylammonium chloride. Other useful cationic surfactants are quaternized protein hydrolysates.

As well as non-ionic organic thickeners with properties similar to wax and non-ionic surfactants, the dye can include the usual cosmetic cationic resins. Particularly preferred are Polyquaternium-6 (poly(dimethyl-diallylammonium chloride)), Polyquaternium-7 (diethyldiallylammonium chloride/acrylamide copolymer), Polyquaternium-10 (cationic cellulose), Polyquaternium-11 (diethyl sulfate of N,N-dimethylaminoethylmethacrylic acid/PVP copolymer), Polyquaternium-22, Polyquaternium-35 and Polyquaternium-37 (trimethylaminoethyl methacrylate chloride polymer), either alone or in mixtures thereof. The total quantity of said cationic resins in the dye can range from about 0.1 to 6% by weight.

For the use of oxidative hair tints, the tints are mixed with an oxidative solution immediately before dyeing the hair, and a sufficient quantity of ready-for-use hair colouring mixture, generally about 60 to 200 grams depending on the thickness and quantity of the hair, is applied.

The mixture of hair dye and oxidant or hair dye alone is left on the hair for 2 to 60 minutes at a temperature ranging from 5 to 50° C., preferably for 35 minutes at 30° C.; the hair is then rinsed with water and dried. If necessary, the hair is washed with shampoo after rinsing and optionally rinsed again with a weak organic acid, such as an aqueous solution of tartaric acid. The hair is then dried.

The hair dye according to the invention gives a deep, protective, delicate color. Due to improved color balancing, all parts of the hair can be dyed, from undamaged roots to split ends.

The dyeing results obtained from the examples below, expressed in L*a*b* values, were measured with a Minolta Chroma Meter CR-200 colorimeter.

In the color space L*a*b*, L* indicates lightness and a* and b* are the color coordinates. a* and b* indicate the color directions: +a* is the direction of red, −a* is the direction of green, +b* is the direction of yellow and −b* is the direction of blue.

Differences in color can be expressed by the ΔE values, which are defined by the following equation:

$$\Delta E = [(\Delta L^*)^2 + (\Delta a^*)^2 + (\Delta b^*)^2]^{1/2}$$

Examples

The ingredients listed in the examples are named according to the INCI nomenclature (European Community Decision 2006/257/EC as amended—International Nomenclature of Cosmetic Ingredients).

The compositions used for the examples reported herein are described in Table 1.

TABLE 1

Composition A is the composition according to the invention.

| Ingredients (INCI) | A* w/w % | B w/w % |
|---|---|---|
| AQUA | Q.s. 100 | Q.s. 100 |
| CETEARYL ALCOHOL | 10 | 10 |
| SODIUM LAURETH SULFATE | 1.5 | 1.5 |
| ETHANOLAMINE | 5 | 5 |
| SODIUM LAURYL SULFATE | 0.5 | 0.5 |
| LAURETH-3 | 2 | 2 |
| 1-HYDROXYETHYL 4.5-DIAMINO PYRAZOLE SULFATE | 1 | 1 |
| Potassium Ethylhexyl/Isotrideceth-8 Phosphate | 1.5 | — |
| m-AMINOPHENOL | 0.455 | 0.455 |
| GLYCERYL STEARATE SE | 0.5 | 0.5 |
| PARFUM | 0.5 | 0.5 |
| CERA ALBA | 0.5 | 0.5 |
| SODIUM SULFITE | 0.5 | 0.5 |
| ERYTHORBIC ACID | 0.4 | 0.4 |
| EDTA | 0.3 | 0.3 |
| SODIUM SULFATE | 0.3 | 0.3 |
| 4-AMINO-2-HYDROXYTOLUENE | 0.338 | 0.338 |
| LIMNANTHES ALBA SEED OIL | 0.2 | 0.2 |
| p-AMINOPHENOL | 0.3 | 0.3 |

Tables 2 and 3 show the % loss values after 12 washes on normal and damaged hair. The hair was dyed with a 1:1.5 ratio between dye and 20-volume activator. The product was left on the hair for 30 minutes at the temperature of 30° C. The hair was the rinsed and dried.

TABLE 2

Comparison of compositions for normal hair after 12 washes

| | % loss of Eab |
|---|---|
| Composition A | 5% |
| Composition B | 15% |

TABLE 3

Comparison of compositions for damaged hair after 12 washes

|  | % loss of Eab |
|---|---|
| Composition A | 36% |
| Composition B | 50% |

Evenness was evaluated on the model after treatment of half the head with the two compositions A and B. The results are set out in Table 4.

TABLE 4

Evenness test on model

| Composition | Root-to-tip evenness test |
|---|---|
| A | High |
| B | Moderate |

We performed also some comparative tests between hair color formulations containing potassium ethylhexyl/isotrideceth-8 phosphate and formulations containing other phosphate esters commonly used to improve the color result and its washing resistance.

We prepared different formulations of the red shade 6.66 intense.

A1 is the formula corresponding to the invention.

TABLE 5

| INGREDIENT NAME | A1 | C | D | E |
|---|---|---|---|---|
| AQUA (WATER) | Up to 100 | Up to 100 | Up to 100 | Up to 100 |
| CETEARYL ALCOHOL | 5 | 5 | 5 | 5 |
| CETEARETH-50 | 3 | 3 | 3 | 3 |
| STEARYL ALCOHOL | 2 | 2 | 2 | 2 |
| PROPYLENE GLYCOL | 1 | 1 | 1 | 1 |
| PEG-40 HYDROGENATED CASTOR OIL | 1 | 1 | 1 | 1 |
| LAURYL ALCOHOL | 2.5 | 2.5 | 2.5 | 2.5 |
| 1-HYDROXYETHYL 4,5-DIAMINO PYRAZOLE SULFATE | 2.5 | 2.5 | 2.5 | 2.5 |
| AMMONIA | 2 | 2 | 2 | 2 |
| ETHANOLAMINE | 1.2 | 1.2 | 1.2 | 1.2 |
| COCAMIDOPROPYL BETAINE | 1 | 1 | 1 | 1 |
| M-AMINOPHENOL | 1.1 | 1.1 | 1.1 | 1.1 |
| PARFUM (FRAGRANCE) | 0.8 | 0.8 | 0.8 | 0.8 |
| DECYLTETRADECANOL | 0.7 | 0.7 | 0.7 | 0.7 |
| POTASSIUM ETHYLHEXYL/ ISOTRIDECETH-8 PHOSPHATE | 0.5 | | | |
| SODIUM SULFITE | 0.4 | 0.4 | 0.4 | 0.4 |
| CI 45410 (ACID RED 92) (RED 28) | 0.4 | 0.4 | 0.4 | 0.4 |
| ERYTHORBIC ACID | 0.3 | 0.3 | 0.3 | 0.3 |
| EDTA | 0.2 | 0.2 | 0.2 | 0.2 |
| 4-AMINO-2-HYDROXYTOLUENE | 0.2 | 0.2 | 0.2 | 0.2 |
| P-AMINOPHENOL | 0.05 | 0.05 | 0.05 | 0.05 |
| HC YELLOW NO. 2 | 0.04 | 0.04 | 0.04 | 0.004 |
| CETETH-10 PHOSPHATE and DICETYL PHOSPHATE | | | 0.5 | |
| OLETH-5 PHOSPHATE and DIOLEYL PHOSPHATE | | | | 0.5 |
|  | 100 | 100 | 100 | 100 |

First of all we evaluated the color result on swatches: caucasian hair with 90% of gray hair; natural blonde hair; yak hair; bleached caucasian hair The different hair color formulations have been mixed in 1:1.5 ratio with the activator Oxid.o 20 vol, left to react on swatches 35 minutes at 29° C. Then the swatches have been washed out and dried with a hair dryer The color result on swatches have been evaluated by people expert in hair coloring. The results are reported in table 6

TABLE 6

| Formula | INGREDIENT | Brightness (average evaluation by 10 experts) | Eveness (average evaluation by 10 experts) |
|---|---|---|---|
| A1 | POTASSIUM ETHYLHEXYL/ ISOTRIDECETH-8 PHOSPHATE | 3.5 | 3.6 |
| C | NO PHOSPHATE ESTERS | 1.5 | 1.8 |
| D | CETETH-10 PHOSPHATE and DICETYL PHOSPHATE | 3.1 | 2.8 |
| E | OLETH-5 PHOSPHATE and DIOLEYL PHOSPHATE | 2.3 | 2.5 |

The scores in table 6 have the following meaning: 1=not satisfactory, 2=sufficient, 3=good, 4=excellent The color result on swatches have been evaluated also using a spectrophotometer CM-2500d with the software SpectraMagic NX.

The results in table 7 are comparative data related to formula A1

TABLE 7

| Type of hair | formula | a*(D65) Evaluation |
|---|---|---|
| blonde | A1 | — |
| blonde | C | 1.97 less red |
| blonde | D | 2.24 less red |
| blonde | E | 2.59 less red |
| bleached | A1 | — |
| bleached | C | 1.82 less red |
| bleached | D | 1.34 less red |
| bleached | E | 2.8 less red |

Also the instrumental test confirms that the inventive formula gives a more brilliant color result We studied also the washing resistance of the formula A1 compared to the others on blonde hair To evaluate color fade we used the dE value. The greater value means more color fade.

TABLE 8

| Type of hair | formula | dE*ab(D65) |
|---|---|---|
| Blonde after 12 washes | A1 | 1.85 |
| Blonde after 12 washes | C | 3.09 |
| Blonde after 12 washes | D | 3.23 |
| Blonde after 12 washes | E | 4.27 |

The data demonstrates that the formula A1 is the more resistant to washes

Tables 9 and 10 show other compositions according to the invention

TABLE 9

| Composition: Ingredients (INCI) | C w/w % | D w/w % | E w/w % | F w/w % | G w/w % | H w/w % | I w/w % |
|---|---|---|---|---|---|---|---|
| AQUA | Q.s. to 100 | Q.s. to 100 | Q.s. to 100 | Q.s. to 100 | Q.s. to 100 | Q.s. to 100 | Q.s. to 100 |
| CETEARYL ALCOHOL | 10 | 10 | 10 | 10 | 10 | 10 | — |
| SODIUM LAURETH SULFATE | 1.5 | 1.5 | 1.5 | 1.5 | 1.5 | 1.5 | — |
| ETHANOLAMINE | 0.1 | 0.1 | 0.1 | 0.1 | 0.1 | 0.1 | 0.1 |
| HYDROXYETHYLCELLULOSE | — | — | — | — | — | — | 1 |
| SODIUM LAURYL SULFATE | 0.5 | 0.5 | 0.5 | 0.5 | 0.5 | 0.5 | — |
| LAURETH-3 | 2 | 2 | 2 | 2 | 2 | 2 | 2 |
| Potassium Ethylhexyl/Isotrideceth-8 Phosphate | 1 | 1.5 | 2 | 0.5 | 2.5 | 10 | 10 |
| GLYCERYL STEARATE SE | 0.5 | 0.5 | 0.5 | 0.5 | 0.5 | 0.5 | 0.5 |
| PARFUM | 0.6 | 0.6 | 0.6 | 0.6 | 0.6 | 0.6 | 0.6 |
| CERA ALBA | 0.5 | 0.5 | 0.5 | 0.5 | 0.5 | 0.5 | 0.5 |
| PENTASODIUM PENTETATE | 0.3 | — | 0.3 | 0.3 | — | — | 0.3 |
| ERYTHORBIC ACID | 0.4 | 0.4 | 0.4 | 0.4 | 0.4 | 0.4 | 0.4 |
| EDTA | — | — | — | — | — | — | — |
| SODIUM SULFATE | — | — | — | — | — | — | — |
| LIMNANTHES ALBA SEED OIL | 0.2 | 0.2 | 0.2 | 0.2 | 0.2 | 0.2 | 0.2 |
| BASIC RED 51 | 1 | — | 1 | 0.2 | — | — | 0.1 |
| BASIC YELLOW 87 | 1 | — | 0.5 | 0.4 | — | — | 0.6 |
| BASIC YELLOW 57 | — | — | — | — | — | — | — |
| BASIC BLUE 124 | 0.1 | — | 0.1 | — | — | — | 0.5 |
| HC BLUE 16 | — | — | 0.5 | 0.1 | — | — | — |
| ACID RED 92 | — | 0.2 | — | — | — | — | — |
| ACID RED 52 | — | 0.3 | — | — | — | — | — |
| HC BLUE 2 | — | — | — | — | — | 1 | 1 |
| HC BLUE 18 | — | 0.1 | — | — | 0.2 | — | — |
| HC RED 18 | — | — | — | — | 0.3 | — | — |
| 3-NITRO-p-HYDROXY-ETHYLAMINOPHENOL | — | — | — | — | — | 1 | 1 |

TABLE 10

| INGREDIENTS (INCI) | L w/w % | M w/w % | N w/w % | O w/w % | P w/w % | Q w/w % | R w/w % | S w/w % | T w/w % | U w/w % |
|---|---|---|---|---|---|---|---|---|---|---|
| AQUA | Q.s. to 100 | Q.s. to 100 | Q.s. to 100 | Q.s. to 100 | Q.s. to 100 | Q.s. to 100 | Q.s. to 100 | Q.s. to 100 | Q.s. to 100 | Q.s. to 100 |
| CETEARYL ALCOHOL | 10 | 10 | 8 | 3 | 20 | 10 | — | 10 | 10 | 10 |
| SODIUM LAURETH SULFATE | 1.5 | 1.5 | 1 | 1 | 1 | 1 | — | 1 | 1 | 1 |
| ETHANOLAMINE | 5 | 5 | 5 | 5 | 5 | 5 | 5 | 5 | 5 | 5 |
| SODIUM LAURYL SULFATE | 0.5 | 0.5 | 0.5 | 0.5 | 0.5 | 0.5 | — | 0.5 | 0.5 | 0.5 |
| LAURETH-3 | 2 | 2 | 2 | 2 | 1 | 3 | — | 1 | 1 | 1 |
| Potassium Ethylhexyl/Isotrideceth-8 Phosphate | 1 | 1.5 | 1 | 0.5 | 1.5 | 2 | 2 | 2 | 2 | 2 |
| GLYCERYL STEARATE SE | 0.5 | 0.5 | 0.5 | 0.5 | 0.5 | 0.5 | 0.5 | 0.5 | 0.5 | 0.5 |
| PARFUM | 0.5 | 0.5 | 0.5 | 0.5 | 0.5 | 0.5 | 0.5 | 0.5 | 0.5 | 0.5 |
| CERA ALBA | 0.5 | 0.5 | 0.5 | 0.5 | 0.5 | 0.5 | 0.5 | 0.5 | 0.5 | 0.5 |
| SODIUM SULFITE | 0.5 | 0.5 | 0.5 | 0.5 | 0.5 | 0.5 | 0.5 | 0.5 | 0.5 | 0.5 |
| ERYTHORBIC ACID | 0.4 | 0.4 | 0.4 | 0.4 | 0.4 | 0.4 | 0.4 | 0.4 | 0.4 | 0.4 |
| EDTA | 0.3 | 0.3 | 0.3 | 0.3 | 0.3 | 0.3 | 0.3 | 0.3 | 0.3 | 0.3 |
| SODIUM SULFATE | 0.3 | 0.3 | 0.3 | 0.3 | 0.3 | 0.3 | 0.3 | 0.3 | 0.3 | 0.3 |
| LIMNANTHES ALBA SEED OIL | 0.2 | 0.2 | 0.2 | 0.2 | 0.2 | 0.2 | 0.2 | 0.2 | 0.2 | 0.2 |
| SODIUM POLYACRYLATE | — | — | — | — | — | — | 0.5 | — | — | — |
| CARBOMER | — | — | — | — | — | — | 0.5 | — | — | — |
| ACRYLATES/METHACRYLAMIDE COPOLYMER | — | — | — | — | — | — | 0.2 | — | — | — |
| TOLUENE-2,5-DIAMINE SULFATE | 0.978 | 0.978 | 0.978 | 0.978 | 0.978 | — | — | — | — | — |
| P-PHENYLENEDIAMINE | 0.2 | 0.2 | 0.2 | 0.2 | 0.2 | — | — | — | — | — |
| 4-CHLORORESORCINOL | 0.01 | 0.01 | 0.01 | 0.01 | 0.01 | — | — | — | — | — |
| N,N-BIS (2-HYDROXYETHYL)-P-PHENYLENEDIAMINE SULFATE | 0.01 | 0.01 | 0.01 | 0.01 | 0.01 | 1.511 | 1.511 | 1.511 | 1.511 | 1.511 |

TABLE 10-continued

| INGREDIENTS (INCI) | L w/w % | M w/w % | N w/w % | O w/w % | P w/w % | Q w/w % | R w/w % | S w/w % | T w/w % | U w/w % |
|---|---|---|---|---|---|---|---|---|---|---|
| HYDROXYETHYL-P-PHENYLENEDIAMINE SULFATE | — | — | — | — | — | 1 | 1 | 1 | 1 | 1 |
| RESORCINOL | 0.01 | 0.01 | 0.01 | 0.01 | 0.01 | — | — | — | — | — |
| 2-METHYL RESORCINOL | 0.01 | 0.01 | 0.01 | 0.01 | 0.01 | 0.05 | 0.05 | 0.05 | 0.05 | 0.05 |
| P-AMINOPHENOL | 0.5 | 0.5 | 0.5 | 0.5 | 0.5 | — | — | — | — | — |
| M-AMINOPHENOL | 0.191 | 0.191 | 0.191 | 0.191 | 0.191 | — | — | — | — | — |
| 4-AMINO-M-CRESOL | 0.001 | 0.001 | 0.001 | 0.001 | 0.001 | 0.1 | 0.1 | 0.1 | 0.1 | 0.1 |
| 2,4-DIAMINOPHENOXY-ETHANOL HCL | 0.3 | 0.3 | 0.3 | 0.3 | 0.3 | 0.2 | 0.2 | 0.2 | 0.2 | 0.2 |
| 5-AMINO-6-CHLORO-O-CRESOL | 0.1 | 0.1 | 0.1 | 0.1 | 0.1 | — | — | — | — | — |
| TOLUENE-2,5-DIAMINE SULFATE | 0.978 | 0.978 | 0.978 | 0.978 | 0.978 | — | — | — | — | — |
| P-PHENYLENDIAMINE | 0.2 | 0.2 | 0.2 | 0.2 | 0.2 | — | — | — | — | — |
| 4-CHLORORESORCINOL | 0.01 | 0.01 | 0.01 | 0.01 | 0.01 | — | — | — | — | — |
| N,N-BIS(2-HYDROXYETHYL)-P-PHENYLENEDIAMINE SULFATE | 0.01 | 0.01 | 0.01 | 0.01 | 0.01 | 1.511 | 1.511 | 1.511 | 1.511 | 1.511 |
| HYDROXYETHYL-P-PHENYLENEDIAMINE SULFATE | — | — | — | — | — | 1 | 1 | 1 | 1 | 1 |
| RESORCINOL | 0.01 | 0.01 | 0.01 | 0.01 | 0.01 | — | — | — | — | — |
| 2-METHYL RESORCINOL | 0.01 | 0.01 | 0.01 | 0.01 | 0.01 | 0.05 | 0.05 | 0.05 | 0.05 | 0.05 |
| P-AMINOPHENOL | 0.5 | 0.5 | 0.5 | 0.5 | 0.5 | — | — | — | — | — |
| M-AMINOPHENOL | 0.191 | 0.191 | 0.191 | 0.191 | 0.191 | — | — | — | — | — |

The invention claimed is:

1. Compositions for dyeing keratin fibers comprising at least one direct and/or one oxidation dye and optionally an activator and further comprising a compound obtained by esterification of phosphoric acid with isooctanol (2-ethylhexanol) and ethoxylated tridecylic alcohoL, wherein the compound formed by esterification of phosphoric acid with isooctanol (2-ethylhexanol) and ethoxylated tridecylic alcohol is Potassium Ethylhexyl/Isotrideceth-8 Phosphate, in amounts of 0.1 to 20% by weight of the total composition.

2. Compositions according to claim 1 wherein the oxidation dyes are selected from:
1-Acetoxy-2-Methylnaphthalene, 5-Amino-4-Chloro-o-Cresol, 4-Amino-m-Cresol, 6-Amino-m-Cresol, 3-Amino-2,4-Dichlorophenol, 6-Amino-2,4-Dichloro-m-Cresol, 3-Amino-2,4-Dichlorophenol, 5-Amino-2,6-Dimethoxy-3-Hydroxypyridine, 5-Amino-2,6-Dimethoxy-3-Hydroxypyridine, 3-Amino-2,6-Dimethylphenol, 2-Amino-5-Ethylphenol, 5-Amino-4-fluoro-2-Methylphenol Sulfate, 2-Amino-4-Hydroxyethylaminoanisole, 2-Amino-4-Hydroxyethylaminoanisole, 2-Amino-3-Hydroxypyridine, 4-Amino-2-Hydroxytoluene, 2-Aminomethyl-p-Aminophenol, 4-Amino-2-Nitrodiphenylamine-2'-Carboxylic Acid, m-Aminophenol, o-Aminophenol, p-Aminophenol, 1,3-Bis-(2,4-Diaminophenoxy)propane, 4,6-Bis(2-Hydroxyethoxy)-m-Phenylenediamine, 2,6-Bis(2-Hydroxyethoxy)-3,5-Pyridinediamine, N,N-Bis(2-Hydroxyethyl)-p-Phenylenediamine, 4-Chloro-2-Aminophenol, 2-Chloro-p-Phenylenediamine, 4-Chlororesorcinol, N-Cyclopentyl-m-Aminophenol, 3,4-Diaminobenzoic Acid, 4,5-Diamino-1-((4-Chlorophenyl)Methyl)-1H-Pyrazole-Sulphate, 2,3-Diaminodihydropyrazolo Pyrazolone Dimethosulphonate, 2,4-Diaminodiphenylamine, 4,4'-Diaminodiphenylamine, 2,4-Diamino-5-Methylphenetole, 2,4-Diamino-5-Methylphenoxyethanol, 4,5-Diamino-1-Methylpyrazole, 2,4-Diaminophenol, 2,4-Diaminophenoxyethanol, 2,6-Diaminopyridine, 2,6-Diamino-3-((Pyridin-3-yl)Azo)Pyridine, N,N-Diethyl-m-Aminophenol, N,N-Diethyl-p-Phenylenediamine, N,N-Diethyltoluene-2,5-Diamine, 2,6-Dihydroxy-3,4-Dimethylpyridine, 2,6-Dihydroxyethylaminotoluene, Dihydroxyindole, Dihydroxyindoline, 2,6-Dimethoxy-3,5-Pyridinediamine, m-Dimethylaminophenyl Urea, N,N-Dimethyl-p-Phenylenediamine, 2,6-Dimethyl-p-Phenylenediamine, N,N-Dimethyl 2,6-Pyridinediamine, 4-Ethoxy-m-Phenylenediamine, 3-Ethylamino-p-Cresol, 4-fluoro-6-Methyl-m-Phenylenediamine, 1-Hexyl 4,5-Diamino Pyrazole Sulphate, Hydroquinone, Hydroxyanthraquinoneaminopropyl Methyl Morpholinium Methosulphate, Hydroxybenzomorpholine, Hydroxyethoxy Aminopyrazolopyridine, Hydroxyethylaminomethyl-p-Aminophenol, 1-Hydroxyethyl 4,5-Diamino Pyrazole, Hydroxyethyl-2,6-Dinitro-p-Anisidine, Hydroxyethyl-3,4-Methylenedioxyaniline, Hydroxyethyl-p-Phenylenediamine, 2-Hydroxyethyl Picramic Acid, 6-Hydroxyindole, Hydroxypropyl Bis(N-Hydroxyethyl-p-Phenylenediamine), Hydroxypropyl-p-Phenylenediamine, Hydroxypyridinone, Isatin, N-Isopropyl 4,5-Diamino Pyrazole, N-Methoxyethyl-p-Phenylenediamine, 6-Methoxy-2-methylamino-3-aminopyridine, 2-Methoxymethyl-p-Aminophenol, 2-Methoxymethyl-p-Phenylenediamine, 2-Methoxy-p-Phenylenediamine, 6-Methoxy-2,3-Pyridinediamine, 4-Methoxytoluene-2,5-Diamine, p-Methylaminophenol, 4-Methylbenzyl 4,5-Diamino Pyrazole, 2,2'-Methylenebis 4-Aminophenol, 3,4-Methylenedioxyaniline, 3,4-Methylenedioxyphenol, 2-Methyl-5-Hydroxyethylaminophenol, Methylimidazoliumpropyl p-Phenylenediamine, 2-Methyl-1-Naphthol, 2-Methylresorcinol, 1,5-Naphthalenediol, 1,7-Naphthalenediol, 2,3-Naphthalenediol, 2,7-Naphthalenediol, 1-Naphthol, 2-Naphthol, PEG-3 2,2'-Di-p-Phenylenediamine, p-Phenetidine, m-Phenylenediamine, p-Phenylenediamine, Phenyl Methyl Pyrazolone, N-Phenyl-p-Phenylenediamine, Picramic Acid, Pyrocatechol, Pyrogallol, Resorcinol, Sodium Picramate, Tetraaminopyrimidine, Tetrahydro-6-Nitroquinoxaline, Tetrahydropyranyl, Resorcinol, Toluene-2,5-Diamine Toluene-2,6-Diamine, Toluene-3,4-Diamine, 2,5,6-Triamino-4-Pyrimidinol, and 1,2,4-Trihydroxybenzene or salts thereof.

3. Compositions according to claim 1 wherein the direct dyes are selected from: Acid green 25, Acid blue 74, Acid blue 3, Acid blue 9, Acid red 18, Acid red 184, Acid red 195, Acid red 27, Acid red 33, Acid red 35, Acid red 51, Acid red 73, Acid red 87, Acid red 92, Acid red 95, Acid violet 43, Acid violet 9, Acid yellow 23, Acid yellow 3, Acid yellow 36, Acid yellow 73, Acid orange 6, Acid orange 7, Acid green 1, Acid green 50, Acid Blue 1, Acid Blue 62, Acid Brown 13, Acid Orange 3, Acid Orange 24, Acid Red 14, Acid Red 35, Acid Red 52, Acid Yellow 1, 2-Amino-6-Chloro-4-Nitrophenol, 4-Amino-2-Nitrodiphenylamine-2'-Carboxylic Acid, 2-Amino-3-Nitrophenol, 2-Amino-4-Nitrophenol, 2-Amino-5-Nitrophenol, 4-Amino-2-Nitrophenol, 4-Amino-3-Nitrophenol, Basic Blue 3, Basic Blue 7, Basic Blue 9, Basic Blue 26, Basic Blue 47, Basic Blue 75, Basic Blue 99, Basic Blue 124, Basic Brown 4, Basic Brown 16, Basic Brown 17, Basic Green 1, Basic Green 4, Basic Orange 1, Basic Orange 2, Basic Orange 31, Basic Red 1, Basic Red 1:1, Basic Red 2, Basic Red 22, Basic Red 46, Basic Red 51, Basic Red 76, Basic Red 118, Basic Violet 1, Basic Violet 2, Basic Violet 3, Basic Violet 4, Basic Violet 10, Basic Violet 11:1, Basic Violet 14, Basic Violet 16, Basic Yellow 28, Basic Yellow 40, Basic Yellow 57, Basic Yellow 87, N,N'-Bis(2-Hydroxyethyl)-2-Nitro-p-Phenylenediamine, 2-Chloro-6-Ethylamino-4-Nitrophenol, 2-Chloro-5-Nitro-N-Hydroxyethyl p-Phenylenediamine, N,N'-Dimethyl-N-Hydroxyethyl-3-Nitro-p-Phenylenediamine, Direct Black 51, Direct Red 23, Direct Red 80, Direct Red 81, Direct Violet 48, Direct Yellow 12, Disperse Black 9, Disperse Blue 1, Disperse Blue 3, Disperse Blue 7, Disperse Blue 377, Disperse Brown 1, Disperse Orange 3, Disperse Red 11, Disperse Red 15, Disperse Red 17, Disperse Violet 1, Disperse Violet 4, Disperse Violet 15, HC Blue No. 2, HC Blue No. 4, HC Blue No. 5, HC Blue No. 6, HC Blue No. 8, HC Blue No. 9, HC Blue No. 10, HC Blue No. 11, HC Blue No. 12, HC Blue No. 13, HC Blue No. 14, HC Blue No. 15, HC Blue No. 16, HC Blue No. 17, HC Blue No. 18, HC Brown No. 1, HC Brown No. 2, HC Green No. 1, HC Orange No. 1, HC Orange No. 2, HC Orange No. 3, HC Orange No. 5, HC Orange No. 6, HC Red No. 1, HC Red No. 3, HC Red No. 7, HC Red No. 8, HC Red No. 9, HC Red No. 10, HC Red No. 11, HC Red No. 13, HC Red No. 14, HC Red No. 15, HC Red No. 17, HC Red No. 18, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, HC Yellow No. 16, HC Yellow No. 17, 2-Hydroxyethylamino-5-Nitroanisole, Hydroxyethyl-2-Nitro-p-Toluidine, 4-Hydroxypropylamino-3-Nitrophenol, 3-Methylamino-4-Nitrophenoxyethanol, 3-Nitro-4-Aminophenoxyethanol, 3-Nitro-p-Cresol, 2-Nitro-5-Glyceryl Methylaniline, 4-Nitroguaiacol, 3-Nitro-p-Hydroxyethylaminophenol, 2-Nitro-N-Hydroxyethyl-p-Anisidine, Nitrophenol, 4-Nitrophenyl Aminoethylurea, 4-Nitro-o-Phenylenediamine, 4-Nitro-m-Phenylenediamine, 4-Nitro-o-Phenylenediamine, 2-Nitro-p-Phenylenediamine, 6-Nitro-2,5-Pyridinediamine, 6-Nitro-o-Toluidine, Pigment Blue 15, Pigment Blue 15:1, Pigment Violet 23, Pigment Yellow 13, Solvent Black 3, Solvent Black 5, Solvent Blue 35, Solvent Yellow 85, Solvent Yellow 172, Tetrabromophenol Blue, Tetrahydro-6-Nitroquinoxaline, Tetrahydropyranyl Resorcinol, natural direct dyes based on lawsone, juglone, alizarin, purpurin, carminic acid, kermesic acid, purpurogallin, protocatechualdehyde, indigo, isatin, curcumin, spinulosine and apigenidine, and henna packs or extracts.

4. Compositions according to claim 1 wherein the activator is selected from hydrogen peroxide, carbamide peroxide, perborates, persulphates and peracids.

5. Compositions according to claim 1, further comprising one or more ingredients selected from pH adjusters, reducing agents, antioxidants, pigments, solvents, surfactants, thickeners, conditioners, film-forming agents, electrolytes, sequestering agents, preservatives and beeswax.

* * * * *